United States Patent
Wang et al.

(10) Patent No.: US 8,168,238 B2
(45) Date of Patent: May 1, 2012

(54) **EXTRACTS OF *AQUILARIA* HULLS AND USE THEREOF IN THE TREATMENT OF CANCER**

(75) Inventors: Ching-Chiung Wang, Pan-Chiao (TW); Lih-Geeng Chen, Keelung (TW); Ting-Lin Chang, Taichung (TW); Chi-Ting Hsieh, Changhua (TW)

(73) Assignee: Taipei Medical University, Taipei (TW)

( * ) Notice: Subject to any disclaimer, the term of this patent is extended or adjusted under 35 U.S.C. 154(b) by 226 days.

(21) Appl. No.: 12/649,180

(22) Filed: Dec. 29, 2009

(65) Prior Publication Data

US 2011/0160152 A1     Jun. 30, 2011

(51) Int. Cl.
*A01N 65/00* (2009.01)
(52) U.S. Cl. ...................................... 424/725
(58) Field of Classification Search .................... None
See application file for complete search history.

(56) References Cited

OTHER PUBLICATIONS

Chen et al, Cucurbitacins and cucurbitane glycosides: structures and biological activities, journal, Nat. Prod. Rep. 2005, 22, pp. 386-399, The Royal Society or Chemistry.
Sturm et al, Analysis of Cucurbitacins in Medicinal Plants by High-Pressure Liquid Chromatography-Mass Spectrometry, Journal, Phytochemical Analysis, 11, pp. 121-127, 2000, John Wiley & Sons, Ltd.
Gao et al, Determination of cucubitacin E-2 glucopyranoside in fructus of cucurbita pepo by HPLC, Journal, Chin Hosp. Pharm. J., 2007, vol. 27, No. 12.
Feng et al, Determination of cucubitacin from cucubita pepo ev dayangua by HPLC, Journal, Journal of chinse Medicinal Materials, 2007.

*Primary Examiner* — Michael Meller
(74) *Attorney, Agent, or Firm* — WPAT, P.C.; Anthony King

(57) ABSTRACT

The invention discloses an ethyl acetate layer of methanol extract of *Aquilaria* hulls for killing cancer cells and treating/preventing cancers and its uses. The extracts of *Aquilaria* hulls has an significant amount of cucurbitacins and these cucurbitacins are effective in killing cancer cells and treating/preventing cancers.

11 Claims, 13 Drawing Sheets
(12 of 13 Drawing Sheet(s) Filed in Color)

5-1

5-2

EXTRACTS OF *AQUILARIA* HULLS AND USE THEREOF IN THE TREATMENT OF CANCER

FIELD OF THE INVENTION

The invention relates to an ethyl acetate layer of methanol extract of *Aquilaria* hulls for killing cancer cells and treating/preventing cancers and its uses. In particular, the extract is from *Aquilaria agallocha* Roxb. and has significant amount of cucurbitacins.

BACKGROUND OF THE INVENTION

The genus *Aquilaria* is an angiosperm taxonomically placed in the Thymelaceaceae family. Fifteen species of *Aquilaria* have been reported and all produce agarwood. The taxonomy of these species is not completely clear and not all species are recognized by taxonomists. Species include *Aquilaria malaccensis, A. agallocha, A. baillonii, A. crassna, A. hirta, A. rostrata, A. beccariana, A. cummingiana, A. filaria, A. khasiana, A. microcarpa, A. grandiflora, A. chinesis* or *A. sinensis, A. borneensis*, and *A. bancana*. *Aquilaria* trees are native to Asia from northern India to Vietnam and Indonesia. They occur particularly in the rain forests of Indonesia, Thailand, Cambodia, Laos, Vietnam, Malaysia, northern India, the Philippines, Borneo and New Guinea. The *Aquilaria* tree is an evergreen that grows up to 30-40 meters high and 60 centimeters in diameter. It bears white flowers that are sweetly scented. The healthy wood of the *Aquilaria* tree is white, soft, even-grained, and not scented when freshly cut. Under certain pathological conditions, the heartwood becomes saturated with resin, and eventually becomes hard to very hard. The best grade of agarwood is hard, nearly black and sinks when placed in water. In general, agarwood lighter in tone is considered inferior as it has smaller amounts of resin.

The natural cucurbitacins constitute a group of diverse triterpenoid substances which are well-known for their bitterness and toxicity. They are characterized by the tetracyclic cucurbitane nucleus skeleton, namely, 19-(10→9 β)-abeo-10 α-lanost-5-ene (also known 9 β-methyl-19-nor lanosta-5-ene), with a variety of oxygenation functionalisies at different positions. Traditionally, the cucurbitacins are arbitrarily divided into twelve categories, incorporating cucurbitacins A-T. It is known in the art that cucurbitacins are cytotoxic and have anti-cancer activity. However, the application potential of cucurbitacins is substantially hindered by their non-specific cytotoxicity, and therefore, only very limited usage is pursued under strict medical control. Cucurbitacins were originally isolated as the bitter principles of the Cucurbitaceae, and were later found to be present, either non-glycosylated or glycosylated, in plants of the families Brassicaceae, Scrophulariaceae, Begoniaceae, Elaeocarpaceae, Datiscaceae, Desfontainiaceae, Polemoniaceae, Primulaceae, Rubiaceae, Sterculiaceae, Rosacease and Thymelacaeceae (Jian Chao Chen et al., Nat. Prod. Rep., 2005, 22, pp. 386-399). Sonja Sturm and Hermann Stuppner applies high-pressure liquid chromatography-mass spectrometry (HPLC-MS) to the analysis of cucurbitacins in medical plants and demonstrates its applicability through the determination of cucurbitacins in *Citrullus colocynthis* (Cucurbitaceae), *Bryonia cretica* ssp. *dioica* (Cucurbitaceae), *Gratiola officinalis* (Scrophulariaceae), *Picrorhiza kurroa* (Scrophulariaceae) and *Iberis umbellate* (Brassicaceae) (Phytochem. Anal. 11, 121-127 (2000)). HPLC methods are established for the simultaneous determination of four bioactive cucurbitacins in *Cucubita pepo* cv *Dayangua* (Cucurbitaceae) (Journal of Chinese Medicinal Materials, 2007, vol. 30, No. 4, pp. 418-420 and Chin Hosp Pharm J, 2007, December, Vol 27, No. 12, pp. 1694-1969).

However, none of the prior art provides information regarding cucurbitacins from *Aquilaria agallocha* or its hulls and the anti-cancer activity thereof.

SUMMARY OF THE INVENTION

The invention provides a *Aquilaria* hull extract for killing cancer cells and treating/preventing cancers comprising an ethyl acetate layer of methanol extract that is obtained by methanol extraction followed by partition with ethyl acetate and water.

The invention also provides a method of killing cancer cells, comprising administering to a subject an effective amount of an extract of the invention whereby the cancer cells can be killed.

The invention also provides a method of treating/preventing cancers, comprising administering to a subject an effective amount of an extract of the invention whereby the cancer can be treated and/or prevented.

The invention also provides a method of inducing apoptosis in cancer cells, comprising administering to a subject an effective amount of an extract of the invention whereby the cancer cells are in apoptosis.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
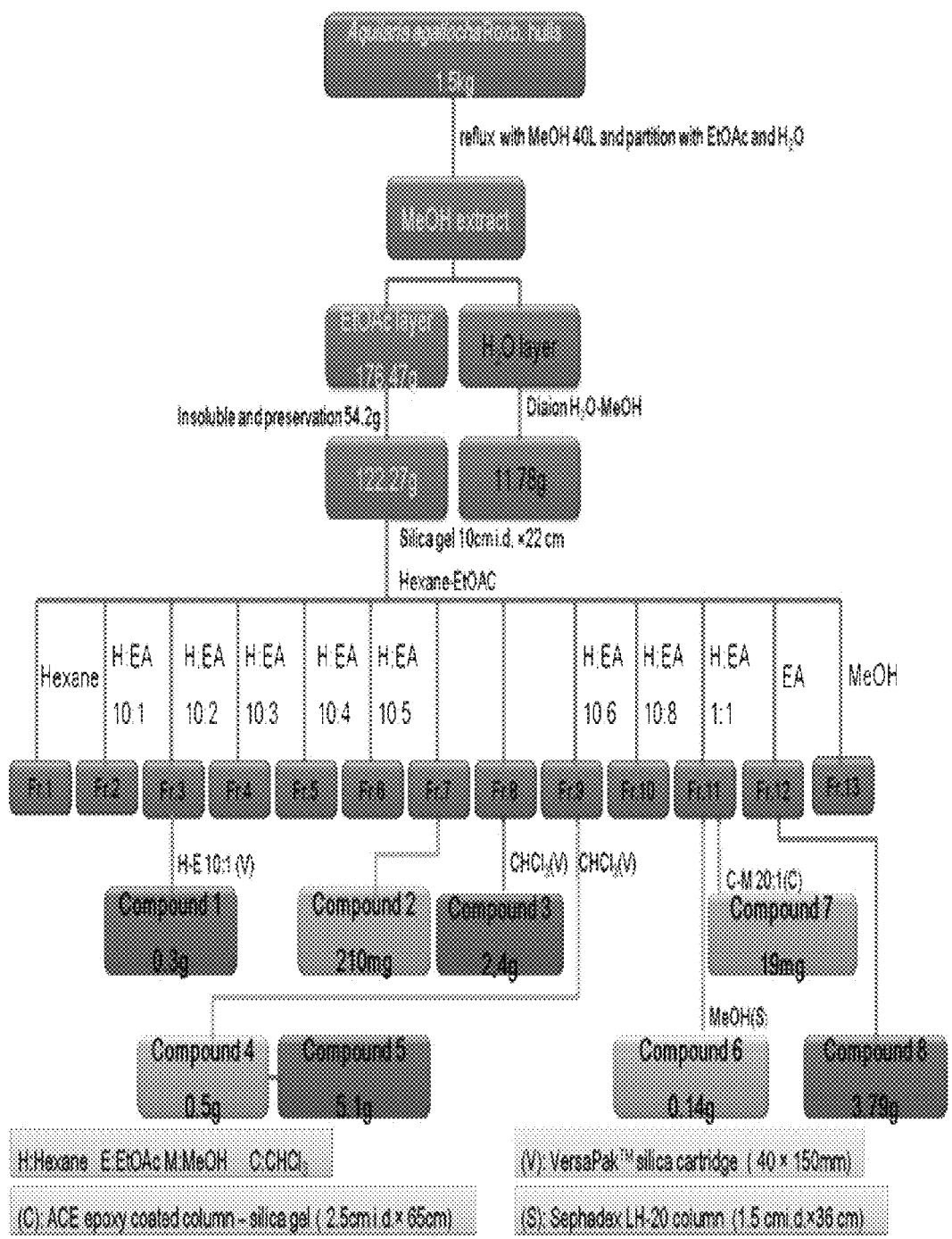
FIG. 1 shows a scheme of separating the active ingredients (compounds 1 to 8) from the *Aquilaria agallocha* Roxb.

The invention discovers that the ethyl acetate layer of methanol extract of *Aquilaria* hulls has a significant amount of cucurbitacins and other active ingredients and these compounds are effective in killing cancer cells, treating/preventing cancers and inducing apoptosis of cancer cells. Furthermore, the ethyl acetate layer of methanol extract of *Aquilaria* hulls is non-toxic.

As used herein, "a" or "an" may mean one or more. As used herein in the claim(s), when used in conjunction with the word "comprising", the words "a" or "an" may mean one or more than one.

"*Aquilaria* hulls" as used herein refers to the woody hull of the fruit of *Aquilaria* tree.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

The invention provides a *Aquilaria* hull extract for killing cancer cells and treating/preventing cancers comprising an ethyl acetate layer of methanol extract that is obtained by methanol extraction followed by partition with ethyl acetate and water. The ethyl acetate layer can be further eluted by mobile phases of (i) hexane-ethyl acetate mixture in a ratio of 1:0, 10:1, 10:2, 10:3, 10:4, 10:5, 10:6, 10:8, 1:1 and 0:1 and (ii) methanol with lo silica column chromatography so that 13 fractions are obtained. The invention found that the Fraction 3 (10:2) specifically contains beta-sitosterol, Fraction 7 (10:5) specifically contains genkwanin, Fraction 8 (10:5) specifically contains cucurbitacin E, Fraction 9 (10:5) specifically contains cucurbitacin I and cucurbitacin E glucoside, Fraction 11 (1:1) specifically contains cucurbitacin I glucoside and Fraction 12 (0:1) specifically contains genkwanin 5-O-glucoside and mangiferin. Beta-sitosterol, genkwanin, cucurbitacin I, cucurbitacin E, mangiferin and their derivatives have anti-cancer activity. The preferred embodiments are shown below:

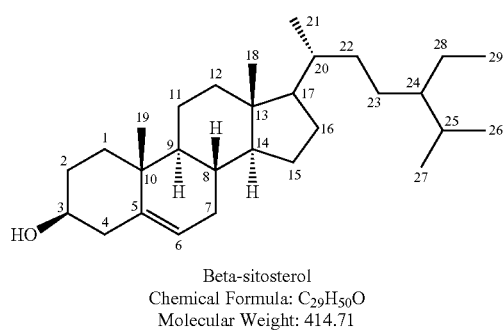

Beta-sitosterol
Chemical Formula: $C_{29}H_{50}O$
Molecular Weight: 414.71

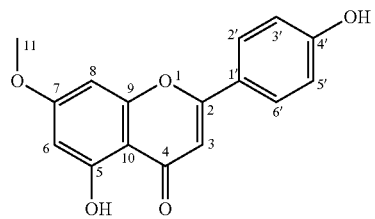

Genkwanin
Chemical Formula: $C_{16}H_{12}O_5$
Molecular Weight: 284.26

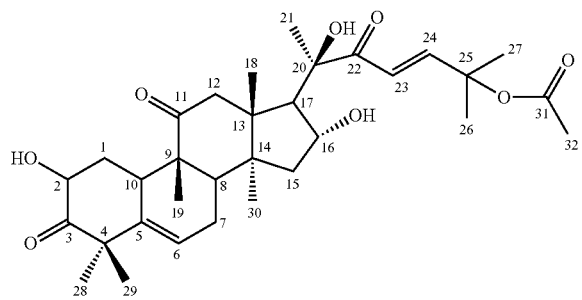

Cucurbitacin E
Chemical Formula: $C_{32}H_{44}O_8$
Molecular Weight: 556.59

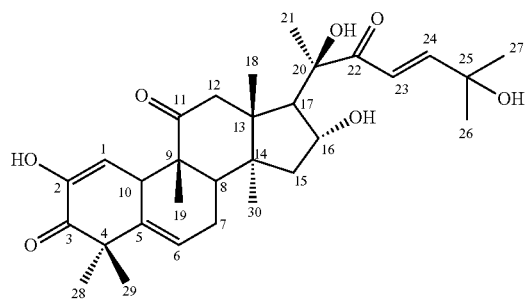

Cucurbitacin E
Chemical Formula: $C_{30}H_{42}O_7$
Molecular Weight: 514.65

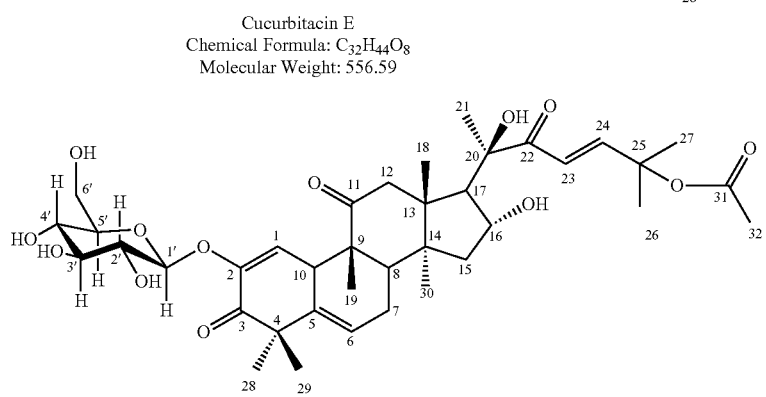

Cucurbitacin E glucoside
Chemical Formula: $C_{38}H_{54}O_{13}$
Molecular Weight: 718.83

-continued

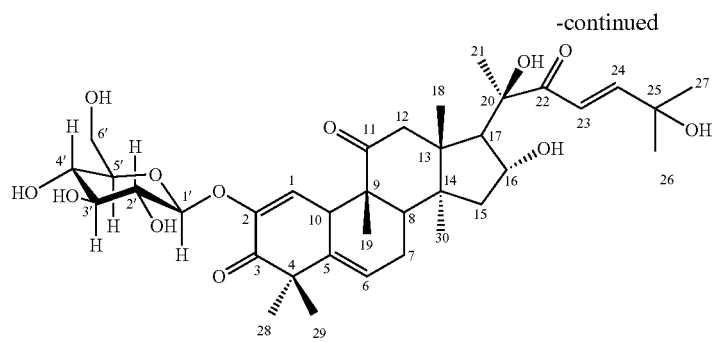

Cucurbitacin I glucoside
Chemical Formula: $C_{36}H_{52}O_{12}$
Molecular Weight: 676.79

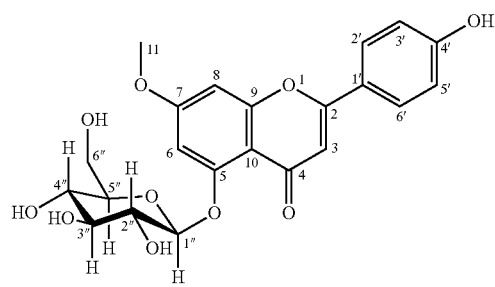

Genkwanin 5-O-glucoside
Chemical Formula: $C_{22}H_{22}O_{10}$
Molecular Weight: 446.40

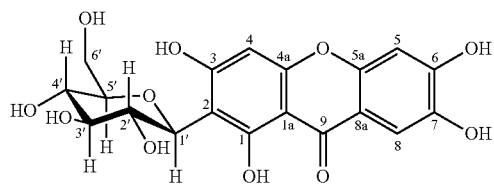

Mangiferin
Chemical Formula: $C_{19}H_{18}O_{11}$
Molecular Weight: 422.34

In one embodiment, the invention provides a *Aquilaria* hull extract for killing cancer cells comprising a fractions 10:5 and 10:6 obtained by methanol extraction, partition with ethyl acetate and water, and elution using a mobile phase of hexane-ethyl acetate mixture with silica gel chromatography. Preferably, the hexane to ethyl acetate mixture is in a ratio of 10:5 or 10:6. Preferably, the fractions 10:5 can be further isolated to obtain genkwanin, cucurbitacin E, cucurbitacin I and cucurbitacin E glucoside. According to a lo further embodiment of the invention, cucurbitacin E and cucurbitacin I are present in the fraction obtained by dissolution of the precipitate in fraction 10:5, elution of the resulting solution by a mobile phase of $CHCl_3$ with silica column chromatography or silica cartridge, desorption of cucurbitacin E and cucurbitacin I with methanol.

According to the preferred embodiment of the invention, a *Aquilaria* hull is obtained from hulls of *Aquilaria agallocha* Roxb., *Aquilaria agallocha* Roxb (Synonyma: *Agallochum malaccense* (Lam.) Kuntze, *Aquilariella malaccensis* (Lam.) Tiegh, *Aquilaria sinensis*, *A. sinensis* (Lour.) Gilg; Common name: agarwood, eaglewood, gaharu, aloeswood) is one of the 15 species of species of *Aquilaria*. *Aquilaria agallocha* Roxb is an evergreen plant of India, China and Tibet, commonly described as aloe wood or agar wood. Traditionally, bark, root and heartwood are used for their medicinal properties as a folk medicine to treat inflammation, arthritis, vomiting, cardiac disorders, cough, asthma, leprosy, anorexia, headache and gout. However, no prior art teaches or suggests that the extract of *Aquilaria* hull is effective in killing cancer cells and treating/preventing cancers.

According to another embodiment of the invention, the ethyl acetate layer of methanol extract of *Aquilaria* hull can be separated by centrifugal partition chromatography (CPC). The ethyl acetate layer of *Aquilaria* hull is dissolved in a solvent system containing chloroform-methanol-water (preferably, their ratio is 6:7:4, v/v/v), subjecting the solvent to centrifugal partition chromatography to isolate cucurbitacins. According to the invention, cucurbitacin I glucoside, cucurbitacin E glucoside, cucurbitacin I and cucurbitacin E can be obtained. According to a further embodiment of the invention, 9 fractions are obtained wherein Fraction 1 was obtained in 0-14 minutes, Fraction 2 containing 82.49% magiferin was obtained in 15-18 minutes, Fraction 3 was obtained in 19-22 minutes, fraction 4 containing 73.54% curcurbitacin I glucoside was obtained in 23-26 minutes, Fraction 5 containing 63.24% curcurbitacin E glucoside was obtained in 27-38 minutes, Fraction 6 containing 80.09% curcurbitacin I was obtained in 39-63 minutes, Fraction 7 containing beta-sitosterol was obtained in 64-65 minutes, Fraction 8 containing 76.87% curcurbitacin E was obtained in 66-75 minutes and Fraction 9 was obtained in last 76-80 minutes. Molecular sieve (gel filtration or gel permeation) chromatography can be further used to increase purity of the above-mentioned compounds.

The extracts of the present invention may be formulated for administration for the treatment of a cancer. In the manufacture of a pharmaceutical formulation according to the invention, the extracts of the present invention are typically admixed with, inter alia, a pharmaceutically acceptable carrier. The carrier must, of course, be acceptable in the sense of being compatible with any other ingredients in the formulation and must not be deleterious to the patient. The carrier may be a solid or a liquid, or both, and is preferably formulated with the extract as a unit-dose formulation. The extract of the invention may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal, parenteral (e.g., subcutaneous, intramuscular, intradermal, inhalational or intravenous) and transdermal administration, although the most suitable route in any given case will depend on the nature and severity of the condition being treated and on the nature of the particular active product used.

Formulations suitable for oral administration may be in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the extract of the invention and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

In addition to the extracts described herein, the present invention also provides useful therapeutic methods and uses. For example, the present invention provides a method of killing cancer cells and a method of treating/preventing cancers. According to one embodiment of the invention, a method of killing cancer cells and treating/preventing cancers is provided, wherein the method comprising administering to a subject an effective amount of an extract of the invention so that the cancer can be treated and/or prevented. According to another embodiment of the invention, a method of inducing apoptosis of cancer cells comprises administering to a subject an effective amount of an extract of the invention so that the cancer is treated and/or prevented. A use of the extract of the invention in killing cancer cells and treating/preventing cancers is also provided. According to one embodiment of the invention, the cancer mentioned herein is selected from the group consisting of colorectal cancer, gastric cancer, prostate cancer, breast cancer, pancreatic cancer, lung cancer, bladder cancer, colon cancer, cervical cancer and hepatocellular carcinoma.

Subjects may be treated by using the extracts of the present invention and are typically human subjects although the methods of the present invention may be useful for veterinary purposes with other subjects, particularly mammalian subjects including, but not limited to, horses, cows, dogs, rabbits, sheep, and the like. The therapeutically effective dosage of any specific compound will vary somewhat from compound to compound, patient to patient, and will depend upon the condition of the patient and the route of delivery. As a general proposition, a dosage from about 50 to about 1,000 mg/kg will have therapeutic efficacy, with still higher dosages potentially employed for oral and/or aerosol administration. Preferably, the dosage is from about 50 to about 800 mg/kg, about 50 to about 600 mg/kg, about 50 to about 500 mg/kg, about 50 to about 300 mg/kg, about 100 to about 300 mg/kg, about 100 to about 500 mg/kg, about 150 to about 500 mg/kg, about 200 to about 500 mg/kg or 250 to about 400 mg/kg.

The present invention also provides medical foods or dietary supplements comprising the extract or the pharmaceutical formulation of the invention, at least one macronutrient selected from the group consisting of protein, carbohydrate and fat, the medical food being compounded for the amelioration of cancer-related disease. Both the dietary supplements and medical foods of the present invention are preferably used in powder form which can be dissolved in a liquid suitable for human consumption, such as water or a fruit juice. The dietary supplements and medical foods of the present invention can, however, be utilized in any suitable form, such as a solid bar, as a paste, gel, tablet, capsule or liquid.

EXAMPLES

Example 1

Extraction of Hulls of *Aquilaria Agallocha* Roxb 1.5 Kg of hulls of *Aquilaria agallocha* Roxb. were oven dried and pressed and then extracted with 40 L of methanol. The resulting solutions were concentrated under reduced pressure, followed by fraction with ethyl acetate and water. The ethyl acetate fraction was mixed with Celite 545 and was separated by silica gel column chromatography (10.5 cm i.d.×95 cm) using a elution gradient of ethyl acetate/n-hexane under low polar elution to high polar elution. The samples were eluted by methanol. Thin layer chromatography (TLC) was conducted to identify the components in each fraction.

The leaves and seeds of *Aquilaria agallocha* Roxb. were extracted with methanol. The stems of *Aquilaria agallocha* Roxb. were extracted with ethyl acetate. The resulting solutions were concentrated under reduced pressure and solved in methanol for HPLC analysis.

Example 2

Isolation of the Compounds of the Invention

The ethyl acetate fraction was separated by silica gel column chromatography (10.5 cm i.d.×22 cm) using a elution gradient of n-hexane/ethyl acetate under low polar elution to high polar elution (hexane:EtOAc 1:0→10:1→10:2→10:3→10:4→10:5→10:6→10:8→4:1→0:1, v/v), and then eluted with methanol. Fraction 3 (10:2) was purified by VersaPak™ silica cartridge (40×150 mm) using hexane:EtOAc (10:1) as mobile phase to obtain about 0.3 g of the compound 1 (β-sitosterol). Fraction 7 (10:5) was filtered to obtain 210 mg of the compounds 2 (genkwanin) (yellow powders). Factions 8 and 9 eluted with hexane-EtoAc (10:5) were further purified by VersaPak™ silica cartridge (40×150 mm) using chloroform as mobile phase to obtain 2.4 g of compound 3 (cucurbitacin E) (crystals or white precipitates) in fraction 8 and 0.5 g of compound 4 (cucrubitacin I) (white crystals) and 5.1 g of compound 5 (cucrubitacin E glucoside) in fraction 9. Fraction 11 obtained from hexane:EtOAC 1:1 eluent was purified by silica gel column chromatography (2.5 cm i.d.×65 cm) using chloroform:methanol (5:1) as mobile phase or by Sephadex LH-20 column (1.5 cm i.d.×36 cm) to obtain 0.14 g of the compound 6 (cucurbitacin I glucoside) (orange solid). Fraction 12 obtained from EtOAc eluent was purified by silica gel column chromatography (2.5 cm i.d.×65 cm) using chloroform:methanol (20:1) as mobile phase to obtain 19 mg of the compound 7 (genkwanin 5-O-glucoside). 3.79 g of the compound 8 (mangiferin) was obtained from the insoluble filtration of fraction 12.

A scheme of separating the active ingredients (compounds 1 to 8) from the *Aquilaria agallocha* Roxb. is represent by FIG. 1.

Example 3

Chemical Structure Identification of the Compounds Contained in *Aquilaria Agallocha* Roxb Extract of the Invention The methanol extract of the hull of *Aquilaria agallocha* Roxb, the ethyl acetate fraction and water fraction thereof, the methanol extract of the leaves of *Aquilaria agallocha* Roxb, the ethyl acetate extract of the stems of *Aquilaria agallocha* Roxb, and the methanol extract of the seeds of *Aquilaria agallocha* Roxb prepared in Example 1 were dissolved in methanol (5 mg/ml or 1 mg/ml) for HPLC analysis.

Figure 2:
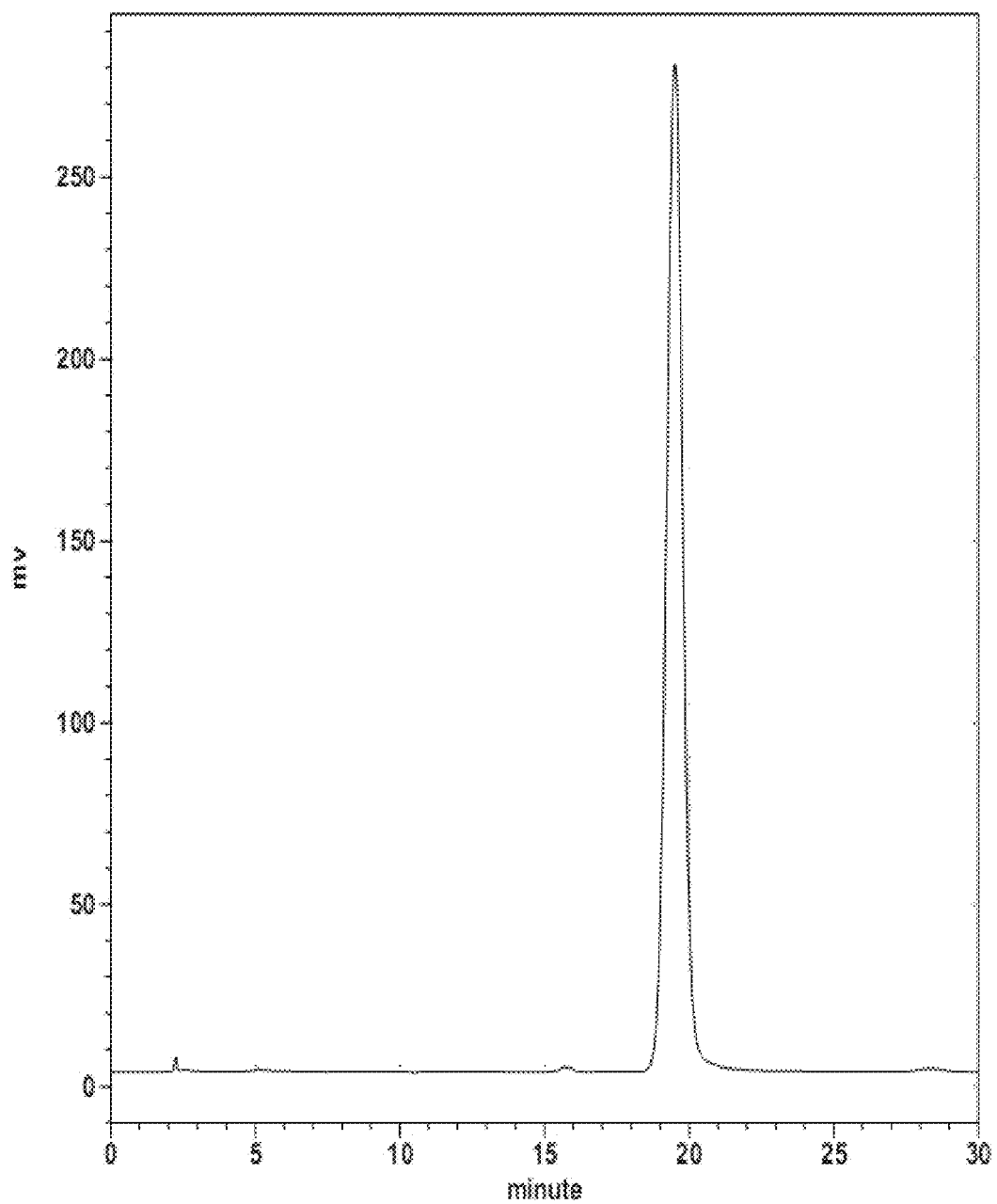
FIG. 2 (2-1 to 2-6) sows the HPLC chromatography of cucurbitacin E (retention time 19.85 min) (FIG. 2-1), cucurbitacin I (retention time 10.33 min) (FIG. 2-2), cucurbitacin E glucoside (retention time 8.76 min) (FIG. 2-3), cucurbitacin I glucose (retention time 5.15 min) (FIG. 2-4), genkwanin glucoside (retention time 4.06 min) (2-5) and mangiferin (retention time 13.40 min) (FIG. 2-6).
Figure 2:
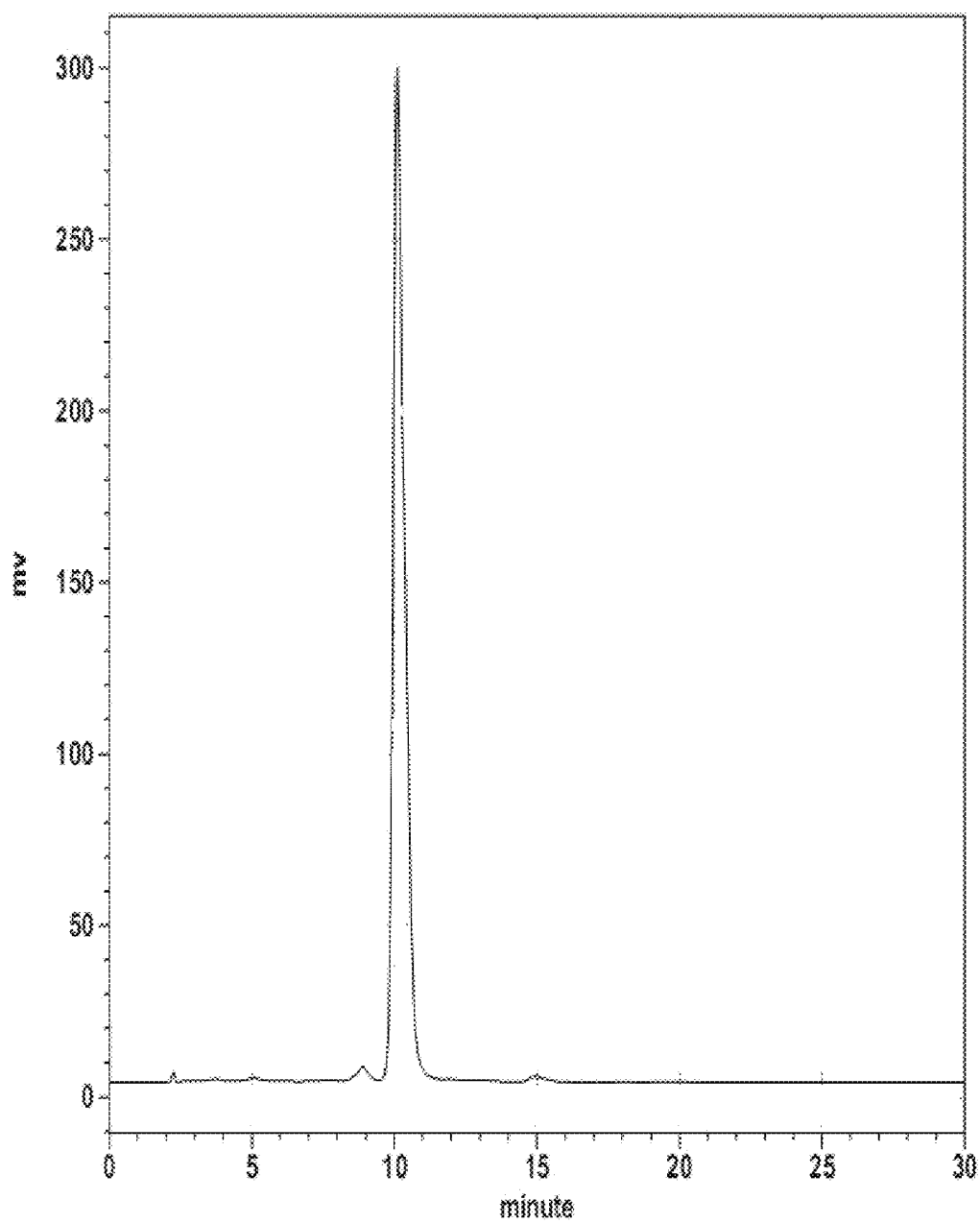
Figure 2:
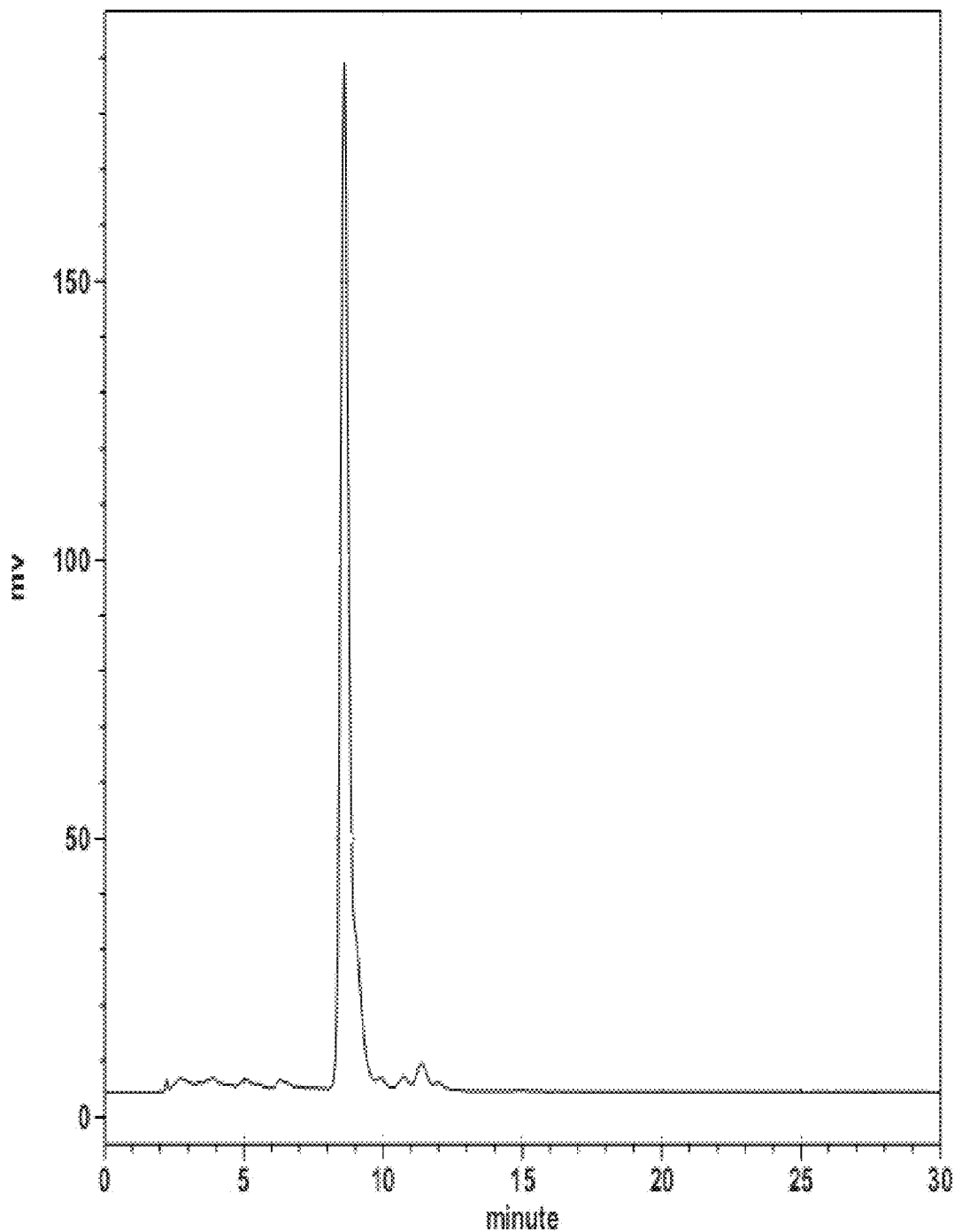
Figure 2:
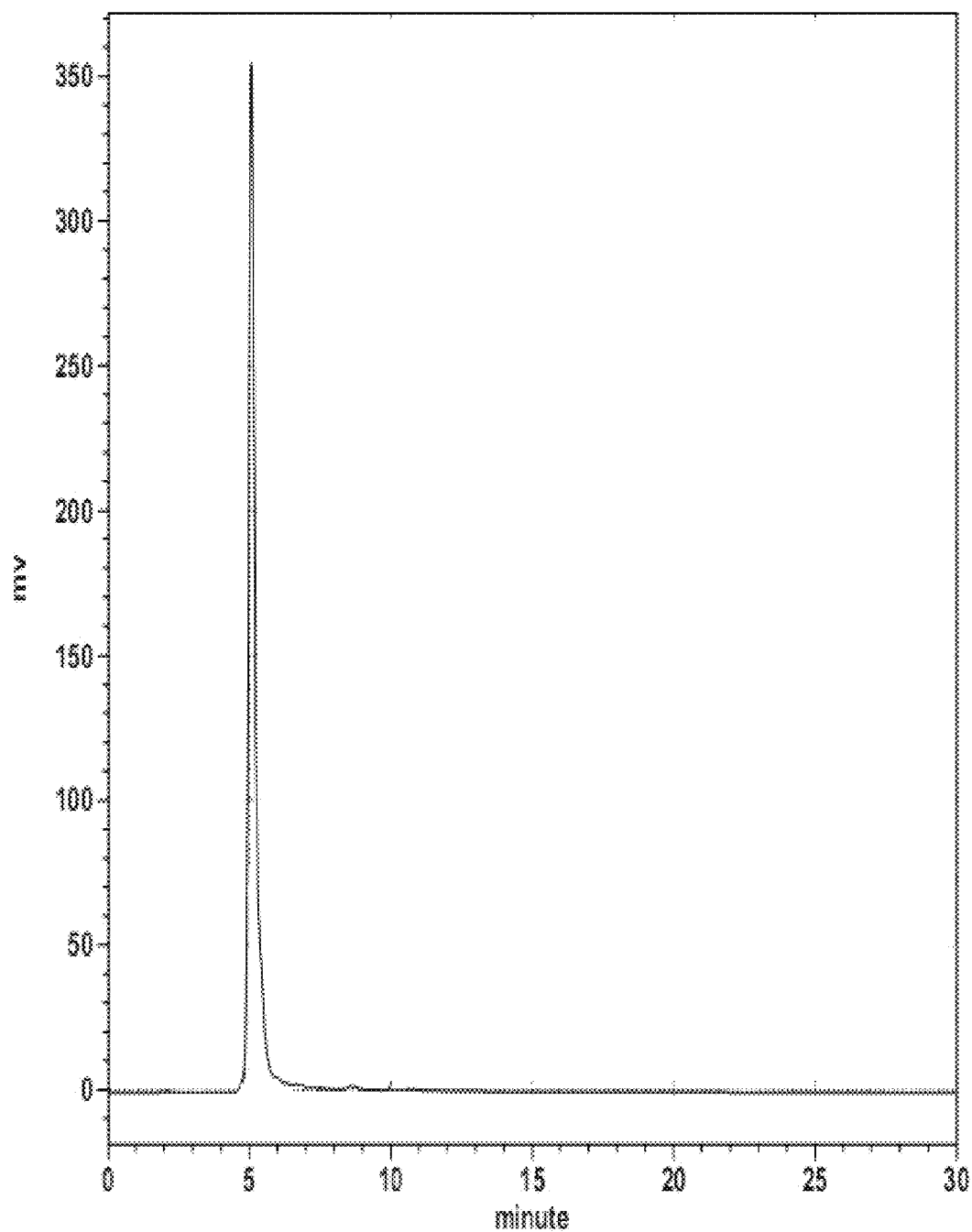
Figure 2:
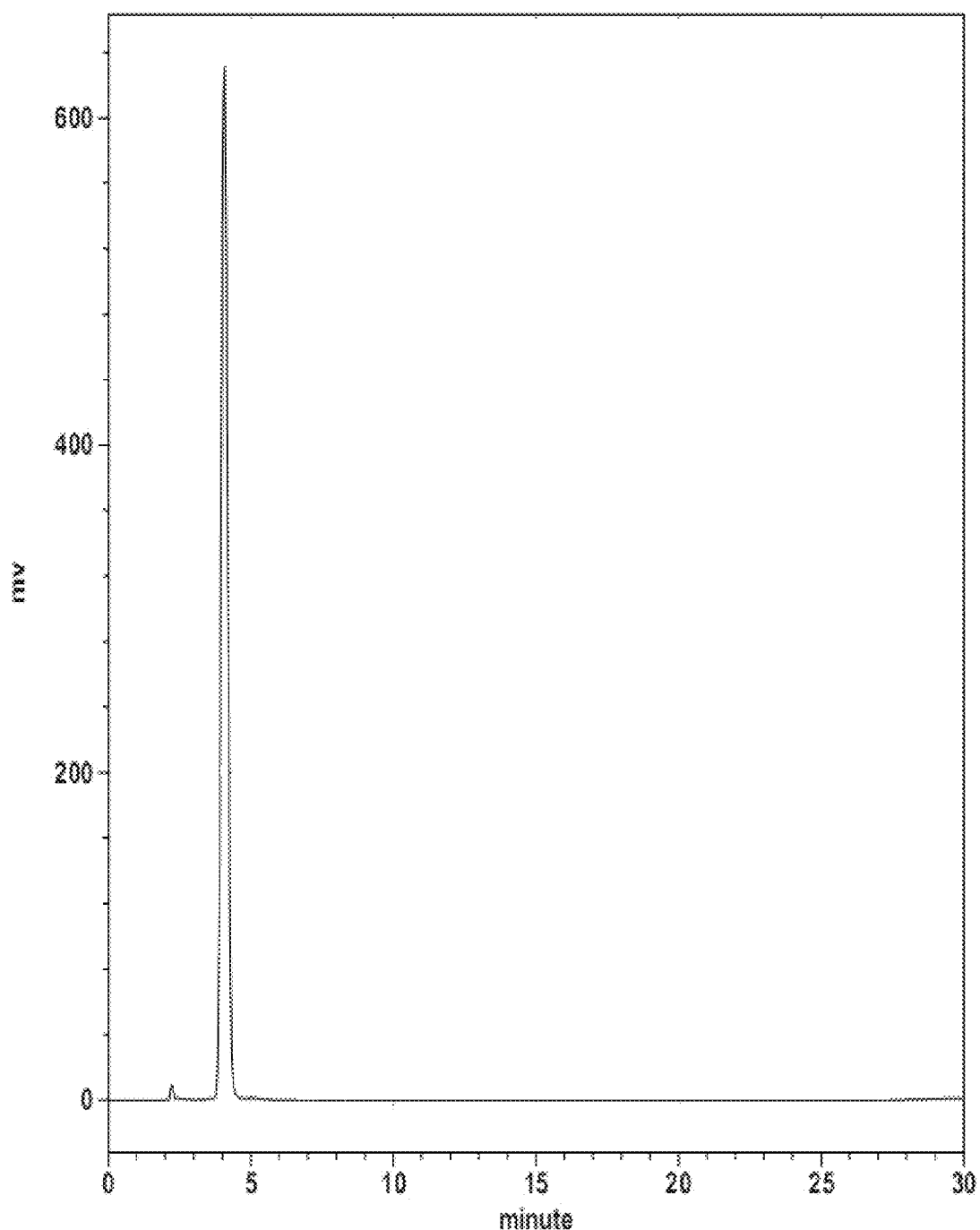
Figure 2:
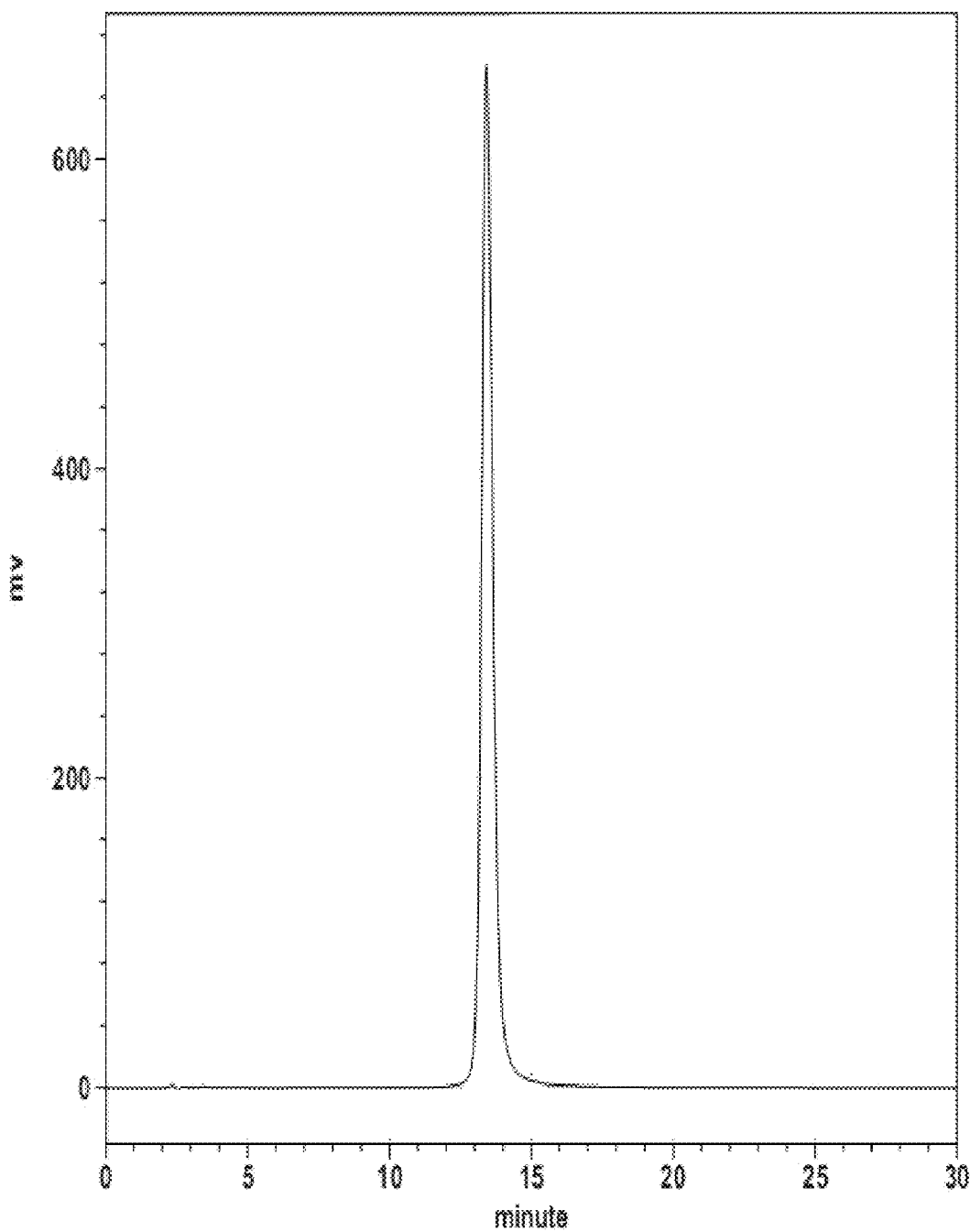

HPLC analysis conditions:
Column: LiChrospher 100 RP-18e (4 mm i.d.×250 mm, 5 μm)
Column temperature: 40° C.
Flow rate: 1.0 ml/min
Wavelength: 236 nm
Mobile phase: 0.05% TFA/MeOH (42:58 in a fixed ratio) for cucurbitacin E (retention time 19.85 min), cucurbitacin I (retention time 10.33 min), cucurbitacin E glucoside (retention time 8.76 min), cucurbitacin I glucose (retention time 5.15 min) and genkwanin glucoside (retention time 4.06 min); 0.05% TFA-MeOH (75:25 in a fixed ratio) for mangiferin (retention time 13.40 min). The HPLC chromatography result is shown in FIG. 2 (2-1 to 2-6).

Compound 1 was detected by GC-MS to determine its molecular weight and 500 MHz NMR to determine its structure. The $^{13}$C NMR spectra data are shown in Table 1. Compound 1 is β-sitosterol.

TABLE 1

$^{13}$C-NMR chemical shift values of compound 1

| position | δC |
| --- | --- |
| 1 | 37.3 |
| 2 | 31.9 |
| 3 | 71.8 |
| 4 | 42.8 |
| 5 | 140.8 |
| 6 | 121.7 |
| 7 | 31.7 |
| 8 | 31.9 |
| 9 | 50.1 |
| 10 | 36.5 |
| 11 | 21.5 |
| 12 | 40.7 |
| 13 | 42.3 |
| 14 | 56.7 |
| 15 | 24.3 |
| 16 | 28.2 |
| 17 | 56.1 |
| 18 | 12.0 |
| 19 | 19.8 |
| 20 | 36.1 |
| 21 | 19.4 |
| 22 | 34.0 |
| 23 | 26.1 |
| 24 | 46.0 |
| 25 | 29.2 |

TABLE 1-continued $^{13}$C-NMR chemical shift values of compound 1

| position | δC |
| --- | --- |
| 26 | 19.0 |
| 27 | 18.9 |
| 28 | 23.1 |
| 29 | 11.9 |

Solvent: Dimethyl sulfoxide-d$_6$,
$^{13}$C-NMR: 126 MHz

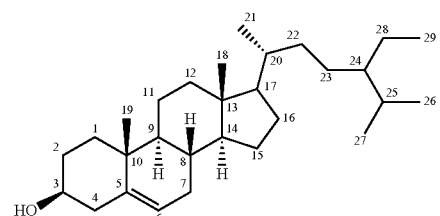

Chemical Formula: $C_{29}H_{50}O$
Molecular Weight: 414.71

Compound 3 was detected by 500 MHz NMR to determine its structure. The results shown in Table 2 reveal that Compound 3 is cucurbitacin E.

TABLE 2

$^1$H- and $^{13}$C-NMR chemical shift values of compound 3

| position | δH (mult., J in Hz) | δC |
| --- | --- | --- |
| 1 | 5.56 (d, 2.4) | 115.6 |
| 2 | — | 145.3 |
| 3 | — | 197.6 |
| 4 | — | 47.3 |
| 5 | — | 136.8 |
| 6 | 5.67 (m) | 119.5 |
| 7 | 1.89 (m) | 23.2 |
|  | 2.25 (m) |  |
| 8 | 1.87 (m) | 41.1 |
| 9 | — | 48.1 |
| 10 | 3.58 (s) | 33.8 |
| 11 | — | 213.7 |
| 12 | 3.35 (m) | 49.9 |
|  | 2.41 (d, 14.6) |  |
| 13 | — | 48.7 |
| 14 | — | 47.9 |
| 15 | 1.68 (m) | 45.6 |
|  | 1.27 (d, 9.4) |  |
| 16 | 4.47 (m) | 69.3 |
| 17 | 2.34 (d, 6.7) | 59.1 |
| 18 | 0.82 (s) | 19.5 |
| 19 | 0.73 (s) | 19.9 |
| 20 | — | 78.6 |
| 21 | 1.26 (s) | 25.4 |
| 22 | — | 203.8 |
| 23 | 6.78 (d, 15.8) | 121.7 |
| 24 | 6.83 (d, 15.8) | 148.6 |
| 25 | — | 79.3 |
| 26 | 1.48 (s) | 26.2 |
| 27 | 1.48 (s) | 26.2 |
| 28 | 1.15 (s) | 27.4 |
| 29 | 1.18 (s) | 20.3 |
| 30 | 1.28 (s) | 17.6 |

TABLE 2-continued

¹H- and ¹³C-NMR chemical shift values of compound 3

| position | δH (mult., J in Hz) | δC |
|---|---|---|
| 31 | — | 169.3 |
| 32 | 1.96 (s) | 21.6 |

Solvent: Dimethyl sulfoxide-$d_6$,
¹H-NMR: 500 MHz,
¹³C-NMR: 126 MHz

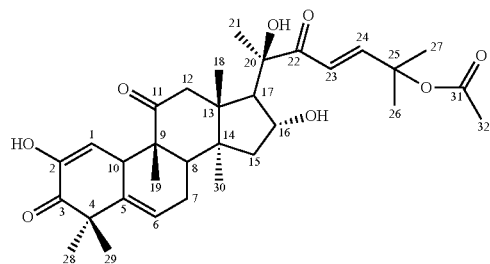

Chemical Formula: $C_{32}H_{44}O_8$
Molecular Weight: 556.69

According to 500 MHz 1-H-NNR and 126 MHz 13C-NMR spectra (see Table 3 below), the framework of compound 4 is very similar to that of compound 3. According to HMBC and HMQC spectra, it was found that the compound 4 lacks an ethyl group on the side chain of cucurbitacin E. Compound 4 is cucurbitacin I.

TABLE 3

¹H- and ¹³C-NMR chemical shift values of compound 3

| position | δH (mult., J in Hz) | δC |
|---|---|---|
| 1 | 5.56 (d, 2.4) | 115.7 |
| 2 | — | 145.2 |
| 3 | — | 197.6 |
| 4 | — | 47.3 |
| 5 | — | 136.8 |
| 6 | 5.67 (m) | 119.5 |
| 7 | 1.89 (m) | 23.2 |
|   | 2.25 (m) |   |
| 8 | 1.87 (m) | 41.1 |
| 9 | — | 48.0 |
| 10 | 3.58 (s) | 33.8 |
| 11 | — | 213.6 |
| 12 | 3.35 (m) | 50.0 |
|   | 2.41 (d, 14.6) |   |
| 13 | — | 48.7 |
| 14 | — | 47.9 |
| 15 | 1.68 (m) | 45.7 |
|   | 1.27 (d, 9.4) |   |
| 16 | 4.46 (m) | 69.2 |
| 17 | 2.34 (d, 6.7) | 58.9 |
| 18 | 0.83 (s) | 19.6 |
| 19 | 0.75 (s) | 20.0 |
| 20 | — | 78.4 |
| 21 | 1.26 (s) | 25.6 |
| 22 | — | 203.9 |
| 23 | 6.78 (d, 15.8) | 120.0 |
| 24 | 6.83 (d, 15.8) | 153.5 |
| 25 | — | 69.4 |
| 26 | 1.25 (s) | 29.1 |
| 27 | 1.89 (s) | 29.3 |
| 28 | 1.15 (s) | 27.4 |

TABLE 3-continued

¹H- and ¹³C-NMR chemical shift values of compound 3

| position | δH (mult., J in Hz) | δC |
|---|---|---|
| 29 | 1.20 (s) | 20.3 |
| 30 | 1.29 (s) | 17.6 |

Solvent: Dimethyl sulfoxide-$d_6$,
¹H-NMR: 500 MHz,
¹³C-NMR: 126 MHz

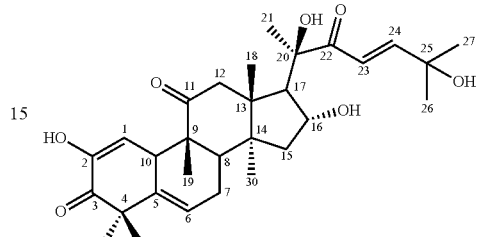

Chemical Formula: $C_{30}H_{42}O_7$
Molecular Weight: 514.65

According to NMR spectra (see Table 4 below), compound 5 is one of cucurbitacin E compounds. The OH on carbon 2 is replaced with a O-glucoside, so compound 5 is cucurbitacin E glucoside.

TABLE 4

¹H- and ¹³C-NMR chemical shift values of compound 5

| position | δH (mult., J in Hz) | δC |
|---|---|---|
| 1 | 5.83 (s) | 122.3 |
| 2 | — | 147.2 |
| 3 | — | 199.8 |
| 4 | — | 51.6 |
| 5 | — | 137.5 |
| 6 | 6.10 (d, 2.4) | 123.5 |
| 7 | 1.88 (m) | 24.0 |
|   | 1.87 (m) |   |
| 8 | 2.1 (m) | 43.2 |
| 9 | — | 49.5 |
| 10 | 3.66 (m) | 36.4 |
| 11 | — | 216.6 |
| 12 | 3.30 (m) | 50.0 |
|   | 2.56 (m) |   |
| 13 | — | 50.4 |
| 14 | — | 50.1 |
| 15 | 1.48 (m) | 46.7 |
|   | 1.89 (m) |   |
| 16 | 4.57 (m) | 71.9 |
| 17 | 2.6 (m) | 60.2 |
| 18 | 1 (s) | 20.6 |
| 19 | 0.89 (s) | 20.8 |
| 20 | — | 80.3 |
| 21 | 1.4 (s) | 25.4 |
| 22 | — | 205.3 |
| 23 | 6.83 (d, 15.8) | 122.6 |
| 24 | 6.96 (d, 15.8) | 151.5 |
| 25 | — | 81.1 |
| 26 | 1.54 (s) | 26.4 |
| 27 | 1.56 (s) | 26.9 |
| 28 | 1.29 (s) | 28.3 |
| 29 | 2.1 (s) | 24.7 |
| 30 | 1.48 (s) | 18.7 |
| 31 | — | 171.8 |
| 32 | 1.99 (s) | 21.9 |
| 1' | 4.63 (d, 7.2) | 101.2 |
| 2' | 3.38 (m) | 74.3 |
| 3' | 3.41 (m) | 77.6 |
| 4' | 3.51 (m) | 70.6 |
| 5' | 3.34 (m) | 78.1 |

TABLE 4-continued $^1$H- and $^{13}$C-NMR chemical shift values of compound 5

| position | δH (mult., J in Hz) | δC |
|---|---|---|
| 6' | 3.85 (dd, 3.6, 12.1)<br>4.03 (dd, 2.2, 12.0) | 61.9 |

Solvent: CD$_3$OD,
$^1$H-NMR: 500 MHz,
$^{13}$C-NMR: 126 MHz

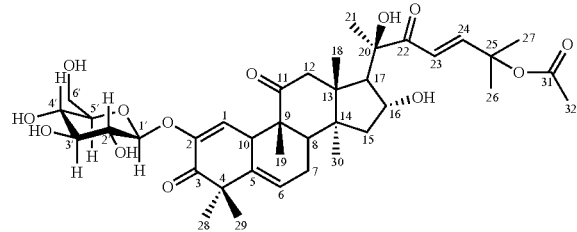

Chemical Formula: C$_{38}$H$_{54}$O$_{13}$
Molecular Weight: 718.83

According to NMR spectra (see Table 5 below), compound 6 is similar to cucurbitacin I in framework structure. Compared with cucurbitacin I, compound 6 has one more glucose. Compound 6 is also similar to cucurbitacin E glucose and lacks an ethyl group. Compound 6 is cucurbitacin I glucoside.

TABLE 5

$^1$H- and $^{13}$C-NMR chemical shift values of compound 6

| position | δH (mult., J in Hz) | δC |
|---|---|---|
| 1 | 5.71 (s) | 120 |
| 2 | — | 145.1 |
| 3 | — | 196 |
| 4 | — | 45.7 |
| 5 | — | 136.3 |
| 6 | 5.8 (d, 1.8) | 120.6 |
| 7 | 1.88 (m)<br>1.87 (m) | 23.3 |
| 8 | 2.1 (m) | 41.1 |
| 9 | — | 49 |
| 10 | 3.66 (m) | 34.3 |
| 11 | — | 213.9 |
| 12 | 3.30 (m)<br>2.56 (m) | 50 |
| 13 | — | 48.7 |
| 14 | — | 48.2 |
| 15 | 1.48 (m)<br>1.89 (m) | 47.4 |
| 16 | 4.57 (m) | 69.2 |
| 17 | 2.6 (m) | 59 |
| 18 | 1 (s) | 19.7 |
| 19 | 0.89 (s) | 20.1 |
| 20 | — | 78.5 |
| 21 | 1.4 (s) | 25.6 |
| 22 | — | 204 |
| 23 | 6.84 (d, 15.5) | 120.1 |
| 24 | 6.74 (d, 14.5) | 153.6 |
| 25 | — | 68.9 |
| 26 | 1.54 (s) | 29.1 |
| 27 | 1.56 (s) | 29.4 |
| 28 | 1.29 (s) | 27.1 |
| 29 | 2.1 (s) | 20.3 |
| 30 | 1.48 (s) | 17.6 |
| 1' | 4.63 (d, 7.2) | 98.7 |
| 2' | 3.38 (m) | 72.7 |
| 3' | 3.41 (m) | 76.8 |
| 4' | 3.51 (m) | 69.4 |
| 5' | 3.34 (m) | 76.9 |

TABLE 5-continued $^1$H- and $^{13}$C-NMR chemical shift values of compound 6

| position | δH (mult., J in Hz) | δC |
|---|---|---|
| 6' | 3.85 (dd, 3.6, 12.1)<br>4.03 (dd, 2.2, 12.0) | 60 |

Solvent: Dimethyl sulfoxide-d$_6$,
$^1$H-NMR: 500 MHz,
$^{13}$C-NMR: 126 MHz

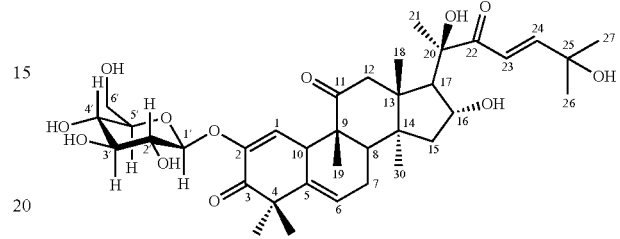

Chemical Formula: C$_{36}$H$_{52}$O$_{12}$
Molecular Weight: 676.79

According to NMR spectra (see Table 6 below), compound 2 is a flavonoid compound-genkwanin particularly in Thymelaeaceae plants. The framework of compound 2 is similar to that of flavonoid compounds but has a OCH3 on C7 (δC 165.0) and chemical shift occurs at 56.0 ppm.

TABLE 6

$^1$H- and $^{13}$C-NMR chemical shift values of compound 2

| position | δH (mult., J in Hz) | δC |
|---|---|---|
| 2 | — | 164.0 |
| 3 | 6.81 (s) | 102.9 |
| 4 | — | 181.9 |
| 5 | — | 161.3 |
| 6 | 6.35 (d, 1.7) | 97.9 |
| 7 | — | 165.0 |
| 8 | 6.74 (d, 1.7) | 92.6 |
| 9 | — | 157.2 |
| 10 | — | 104.6 |
| 11 | 3.85 (s) | 56.0 |
| 1' | — | 120.9 |
| 2' | 7.93 (d, 8.6) | 128.5 |
| 3' | 6.92 (d, 8.6) | 115.9 |
| 4' | — | 161.1 |
| 5' | 6.92 (d, 8.6) | 115.9 |
| 6' | 7.93 (d, 8.6) | 128.5 |

Solvent: Dimethyl sulfoxide-d$_6$,
$^1$H-NMR: 500 MHz,
$^{13}$C-NMR: 126 MHz

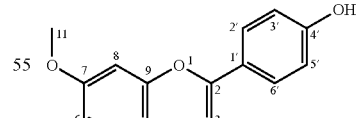

Chemical Formula: C$_{16}$H$_{12}$O$_5$
Molecular Weight: 284.26

According to NMR spectra (see Table 7 below), compound 7 has a framework of a flavonoid compound genkwanin, which further has a substituent O-glucoside on C5 (δ 102.7). Compound 7 is genkwanin 5-O-glucoside.

TABLE 7

$^1$H- and $^{13}$C-NMR chemical shift values of compound 7

| position | δH (mult., J in Hz) | δC |
|---|---|---|
| 2 | — | 161.4 |
| 3 | 6.70 (s) | 105.6 |
| 4 | — | 176.9 |
| 5 | — | 158.4 |
| 6 | 7.05 (d, 1.9) | 96.6 |
| 7 | — | 163.5 |
| 8 | 6.90 (d, 2.4) | 103.5 |
| 9 | — | 158.2 |
| 10 | — | 109.3 |
| 11 | 3.89 (s) | 56.0 |
| 1' | — | 121.0 |
| 2' | 7.91 (d, 8.6) | 128.1 |
| 3' | 6.90 (d, 8.3) | 116.0 |
| 4' | — | 158.2 |
| 5' | 6.90 (d, 8.3) | 116.0 |
| 6' | 7.91 (d, 7.6) | 128.1 |
| 1" | 4.77 (d, 7.6) | 104.2 |
| 2" | 3.28 (overlapped with DHO) | 73.6 |
| 3" | 3.33 (overlapped with DHO) | 75.7 |
| 4" | 3.16 (d, 9.1) | 69.9 |
| 5" | 3.34 (overlapped with DHO) | 77.6 |
| 6" | 3.74 (d, 11.1)<br>3.48 (dd, 6.4, 6.4) | 60.9 |

Solvent: Dimethyl sulfoxide-$d_6$,
$^1$H-NMR: 500 MHz,
$^{13}$C-NMR: 126 MHz

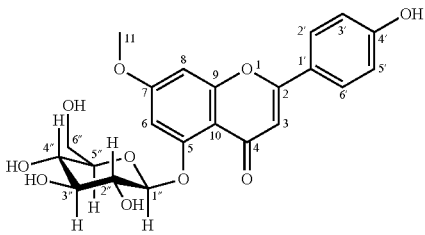

Chemical Formula: $C_{22}H_{22}O_{10}$
Molecular Weight: 446.40

According to NMR spectra (see Table 8 below), compound 8 is a xanthone structure, in which a C-glucoside is attached to carbon 2. From HMBC and $^1$H-$^1$H COSY, it can be deduced that Compound 8 is mangiferin.

TABLE 8

$^1$H- and $^{13}$C-NMR chemical shift values of compound 8

| position | δH (mult., J in Hz) | δC |
|---|---|---|
| 1a | — | 150.8 |
| 1 | — | 161.8 |
| 2 | — | 107.6 |
| 3 | — | 163.8 |
| 4 | 6.36 (s) | 93.3 |
| 4a | — | 156.2 |
| 5a | — | 101.3 |
| 5 | 6.85 (s) | 102.5 |
| 6 | — | 154.3 |
| 7 | — | 143.8 |
| 8a | — | 111.5 |
| 8 | 7.37 (s) | 107.9 |
| 9 | — | 179.0 |
| 1' | 4.58 (d, 9.8) | 73.1 |
| 2' | 4.03 (t, 9.0) | 70.3 |
| 3' | 3.15 (overlapped with DHO) | 79.0 |
| 4' | 3.11 (overlapped with DHO) | 70.6 |
| 5' | 3.19 (overlapped with DHO) | 81.5 |
| 6' | 3.68 (d, 11.3),<br>3.41 (dd, 5.8, 5.8) | 61.5 |

Solvent: Dimethyl sulfoxide-$d_6$,
$^{13}$C-NMR: 126 MHz

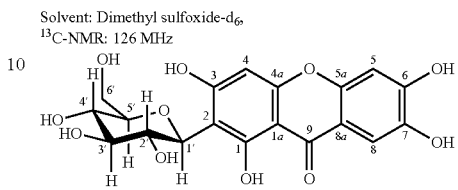

Chemical Formula: $C_{19}H_{18}O_{11}$
Molecular Weight: 422.34

Example 5

Figure 3:
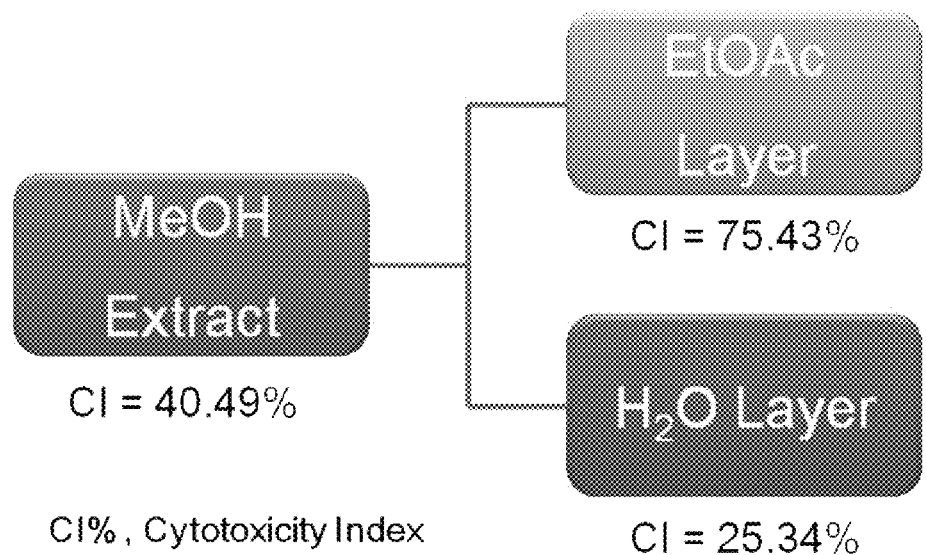
FIG. 3 shows that the ethyl acetate fraction of the *Aquilaria agallocha* Roxb showed better toxicity than the water fraction did.

Effect of Cucurbitacin E and I in Extract of *Aquilaria Agallocha* Roxb. Hulls on Cell Toxicity The effects of cucurbitacin E and I in the extract of *Aquilaria agallocha* Roxb. hulls on cell toxicity in HT29 cells were tested. HT cells were treated with the diluted cucrubitacin E and I (100-1.56 μg/ml). After the cells were treated for 24 hours, cell viability was determined by MTT assay, which quantitatively measures the metabolic activity of living cells. The results showed that cucurbitacin E and I concentrations above 14.1 and 15.8 μM respectively greatly reduced cell viability in HT29 cells. Please see Table 9. The results clearly indicate that both cucurbitacin E and I possess potent toxicity towards HT29 cancer cells. Moreover, when HT29 cells were incubated with 100 μg/ml of each ethyl fraction and water fraction of the methanol extract of hulls of *Aquilaria agallocha* Roxb. of the present invention for 24 hours, the ethyl acetate fraction showed better toxicity than the water fraction did (see FIG. 3)

In addition to HT29 cells, P-388 leukemia cells were also determined by MTT assay. The results showed that cucurbitacin E and I concentrations above 6.5 and 7.4 μM respectively inhibited cell proliferation in P-388 cells. Please see Table 9.

TABLE 9

IC$_{50}$ of cucurbitacin E and Cucurbitacin I on HT29 and P-388 cells

| | IC$_{50}$ (μg/ml) | |
|---|---|---|
| | HT29 cells | P-388 cells |
| Cucurbitacin E | 14.1 | 6.5 |
| Cucurbitacin I | 15.8 | 7.4 |

Example 6

Figure 4:
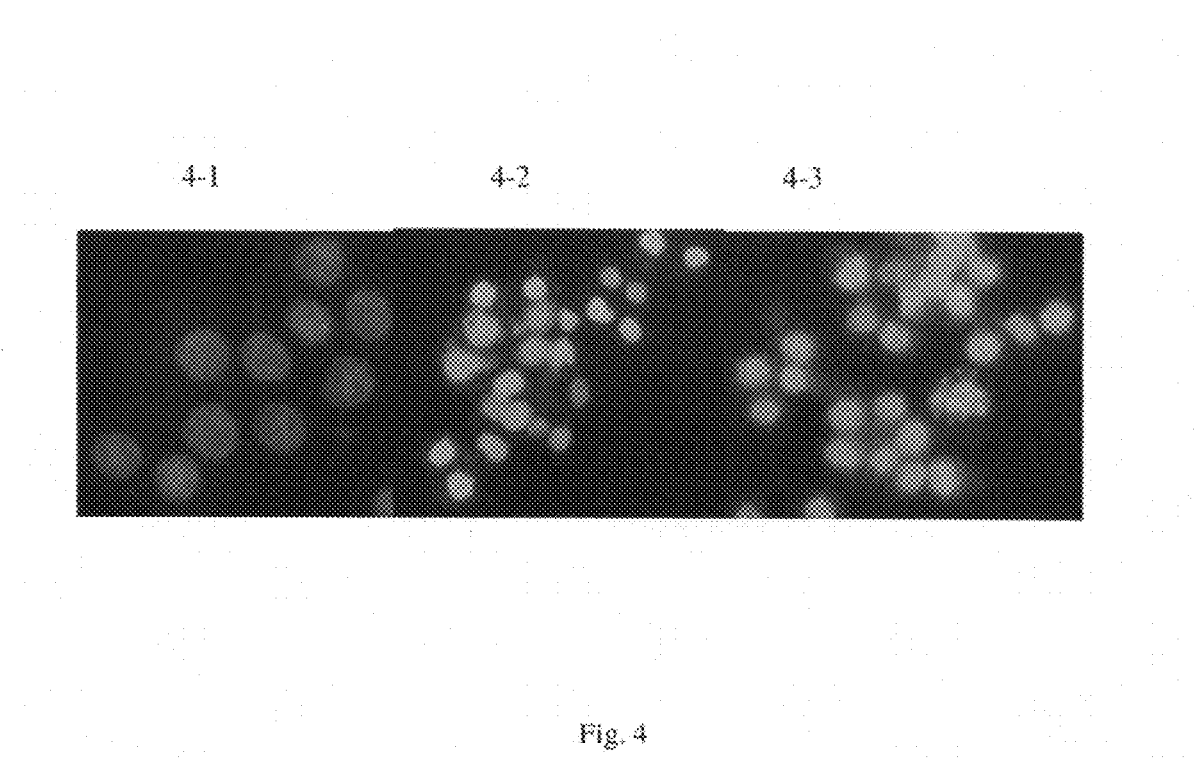
FIG. 4 (4-1 to 4-3) shows that the nucleus were squeezed and the chromatin was condensed as the concentrations of cucurbitachin E and I increased.

Effect of Cucurbitacin E and Cucurbitacin I in Extract of *Aquilaria Agallocha* Roxb. Hulls on Cell Morphology of HT29 Cells The effects of cucurbitacin E and I in the extract of *Aquilaria agallocha* Roxb. hulls on cell morphology in HT29 cells were tested. HT cells were treated with cucurbitacin E or I with different concentrations for 24 hours and stained by 10% Giemsa. The changes in the HT cells were determined under optical microscope and are shown in FIG. 4 (4-1 to 4-3), which indicate that the nucleus were squeezed and the chromatin was condensed as the concentrations of cucurbitachin E and I increased.

Example 7

Figure 5:
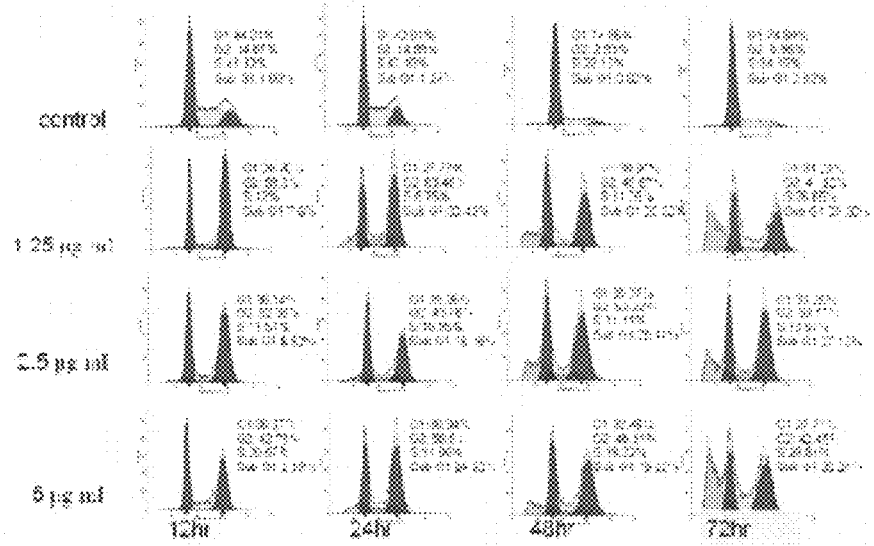
FIG. 5 (5-1 to 5-2) shows the effects of *Aquilaria agallocha* Roxb. extract (cucurbitacin E and I) on the cell cycle distribution of HT29 cells.
Figure 5:
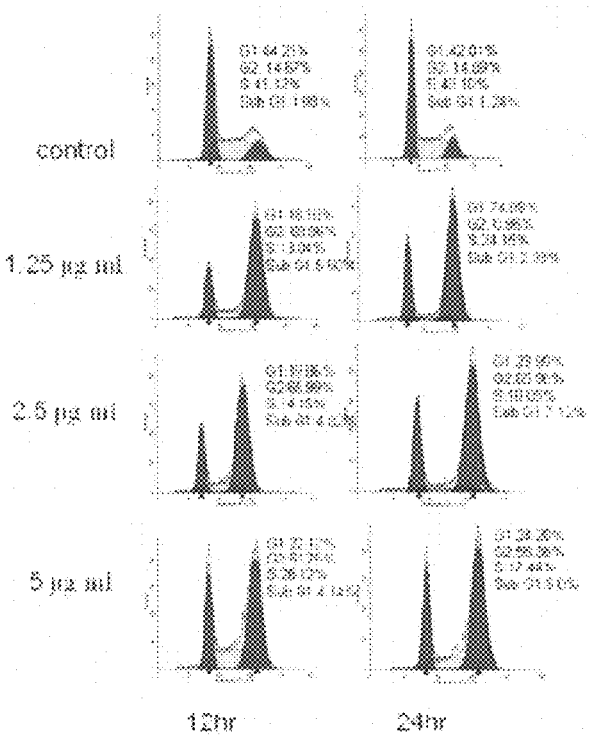

Effect of Cucurbitacin E and Cucurbitacin I in Extract of *Aquilaria Agallocha* Roxb. Hulls on Cell Cycle of HT29 Cells The cell cycle of treated cells was examined by flow cytometry. The effects of cucurbitacin E and I in the extract of *Aquilaria agallocha* Roxb. hulls on the cell cycle distribution of HT29 cells are shown in FIG. 5 (5-1 to 5-2). The alteration of cell cycle profiles in HT29 cells upon cucurbitacin E and I treatment was dose-dependent. In HT29 cells, the sub-G1 populations increased as the concentrations of cucurbitacin E and I increased, which indicates that the treatment of cucurbitacin E and I would increase cell death.

Example 8

Effect of Administration of Extract of *Aquilaria Agallocha* Roxb Hulls to CDF1 Mice The potential of the extract of hulls of *Aquilaria agallocha* Roxb to exhibit the progress of the cancers in vivo was tested in CDF1 mice with P-388D1. Male DBA mice and female BALB/c mice were purchased from National Science Council, Taipei, Taiwan and were bred by the inventors. After mating, the first generation of male $CDF_1$ (eight weeks of age weighing 25±2 g) were obtained for the research. To induce cancer, 0.2 ml of $1\times10^6$ P-388 cells/ml were subcutaneously inoculated to the abdominal cavity of each mouse. One hour after the inoculation, mice were assigned to three groups that received solvent control (Daunorubicin 1 mg/kg/day) or extract of hulls of *Aquilaria agallocha* Roxb at different doses (15 and 30 mg/kg/day) by subcutaneously administration for 9 days. Body weight was measured and shown in FIG. 6. The survival days of the tested mice are shown in Table 10.

TABLE 10

Survival days of mice receiving extract of hulls of *Aquilaria agallocha* Roxb at different doses (15 and 30 mg/kg/day)

| Group | Survival days | | | | | median | ILS % |
|---|---|---|---|---|---|---|---|
| | 1 | 2 | 3 | 4 | 5 | | |
| Control | 18 | 18 | 18 | 22 | 25 | 18 | — |
| 15 mg/kg | 19 | 19 | 20 | 21 | 23 | 20 | 11.10% |
| 30 mg/kg | 18 | 25 | 26 | 27 | 29 | 26* | 44.40% |

Figure 6:
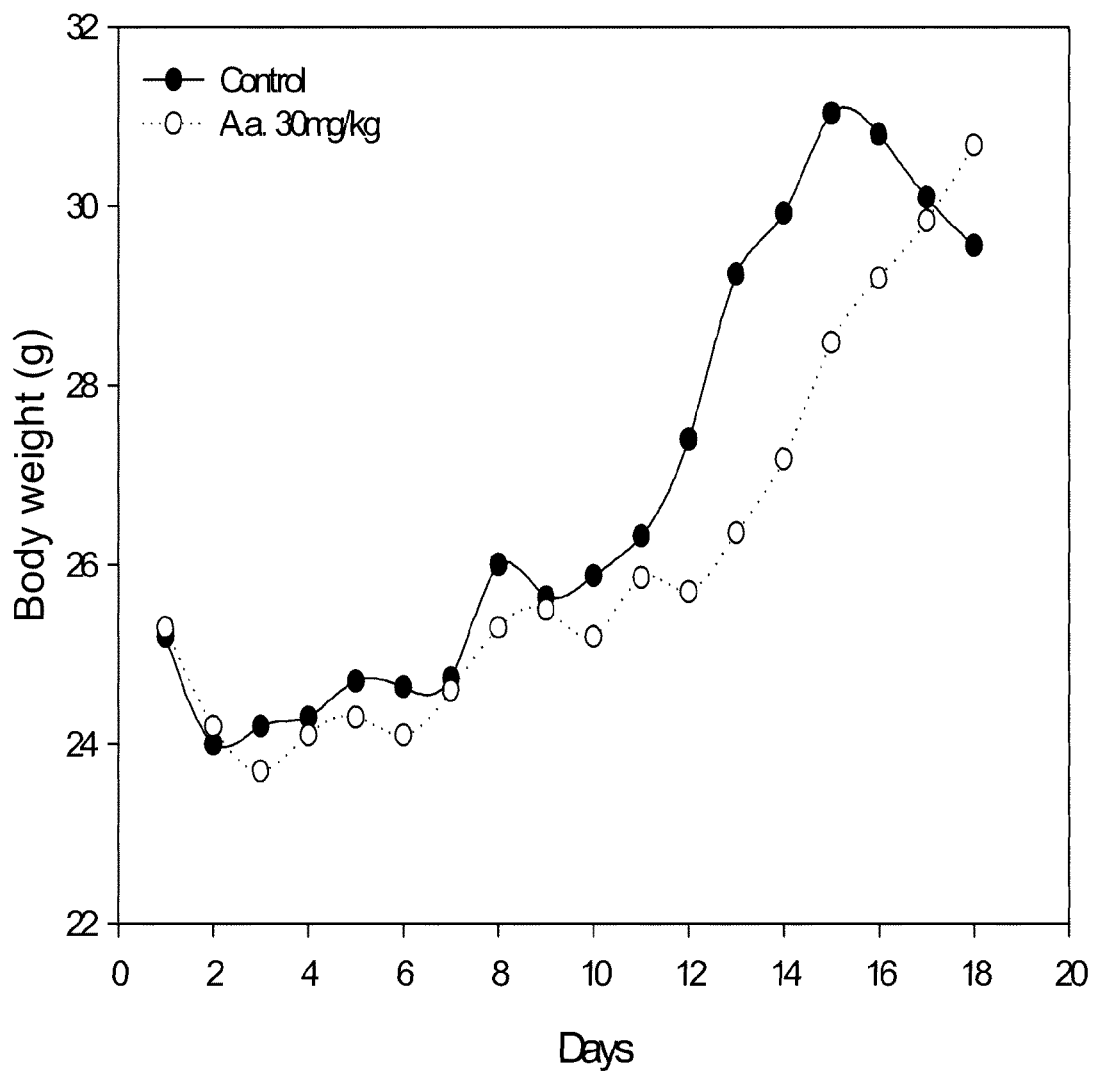
FIG. 6 shows the dose of 30/mg/kg of the extract of the present invention significantly inhibited the progress of ascites.

Student's-t test: *p < 0.05
The percentage increase in life span
ILS % = [(T − C)/C] × 100%
Control: DMSO (0.1%)
T: the mean survival days of the treated group
C: the mean survival days of the control group Results revealed that the administration of the extract of hulls of *Aquilaria agallocha* Roxb of the present invention significantly increased the survival days of the mice. The effect of the extract of the present invention on life span is dose-dependent. As shown in FIG. 6, the dose of 30/mg/kg of the extract of the present invention significantly inhibited the progress of ascites.

Example 9

Effect of Extract of *Aquilaria Agallocha* Roxb. Hulls on Cell Toxicity

The effects of the extract of *Aquilaria agallocha* Roxb. hulls on cell toxicity in T24 cells (human bladder carcinoma cells), HT29 cells (human colon adenocarcinoma cells), HeLa cells (cervical carcinoma cells), AGS cells (gastric epithelial cancer cells) and Hep G2 lo cells (human hepatocellular liver carcinoma cells) were tested. The above-mentioned cells were treated with the extract of *Aquilaria agallocha* Roxb. hulls. The procedures of the cell toxicity test were the same as those mentioned in Example 5. The $IC_{50}$ values of the extract of *Aquilaria agallocha* Roxb. hulls on the above cells are shown in below table 11.

| | IC50 (µg/ml) | | | | |
|---|---|---|---|---|---|
| | T24 | HT-29 | HeLa | AGS | Hep G2 |
| extract of *Aquilaria agallocha* Roxb. hulls | 17.82 | 18.5 | 35.19 | 43.13 | 58.69 |

Example 10

Isolation of Cucurbitacins from Ethyl Acetate Layer of Methanol Extract of *Aquilaria Agallocha* Roxb Hulls by Centrifugal Partition Chromatography (CPC)

Figure 7:
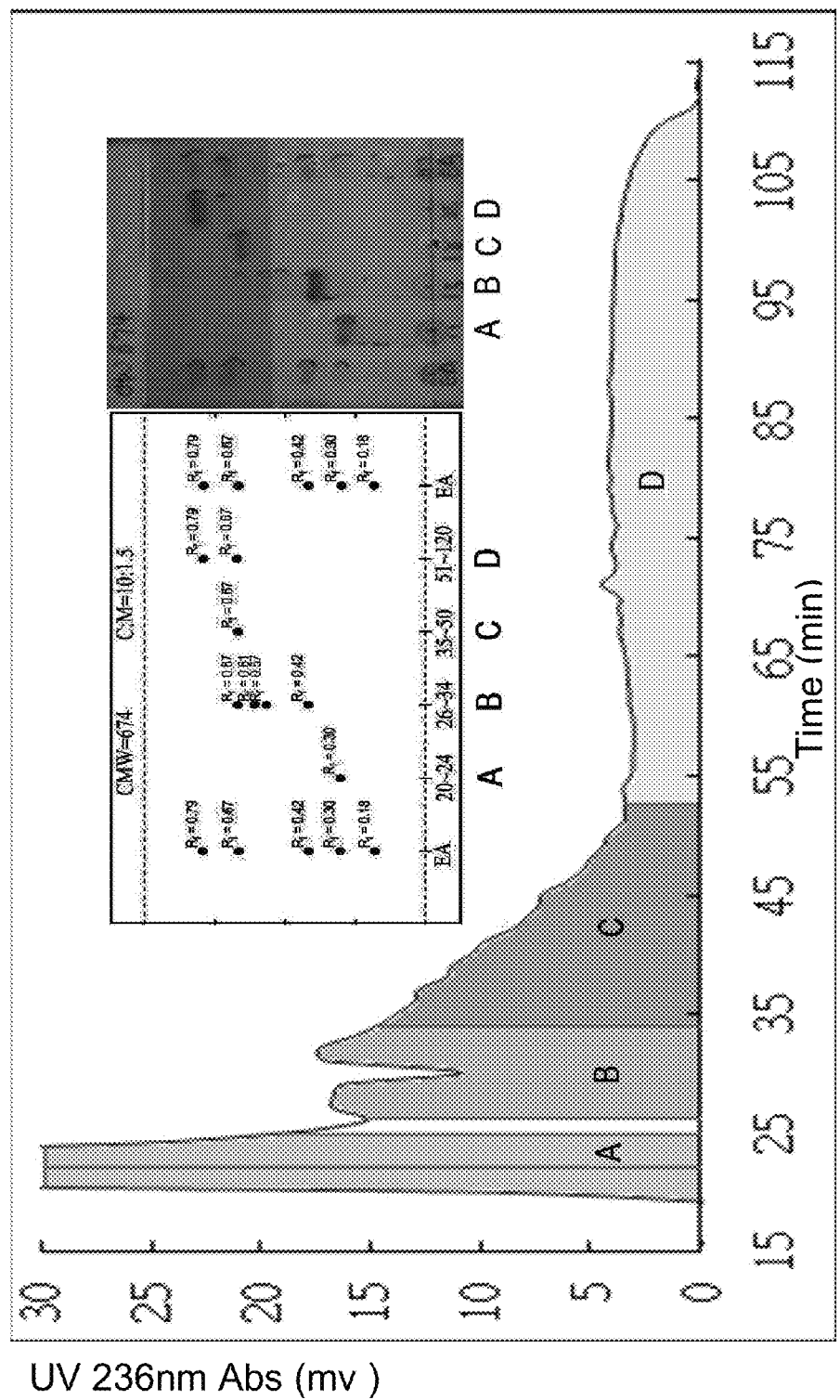
FIG. 7 shows the centrifugal partition chromatography diagram using chloroform-methanol-water solvent system.
Figure 8:
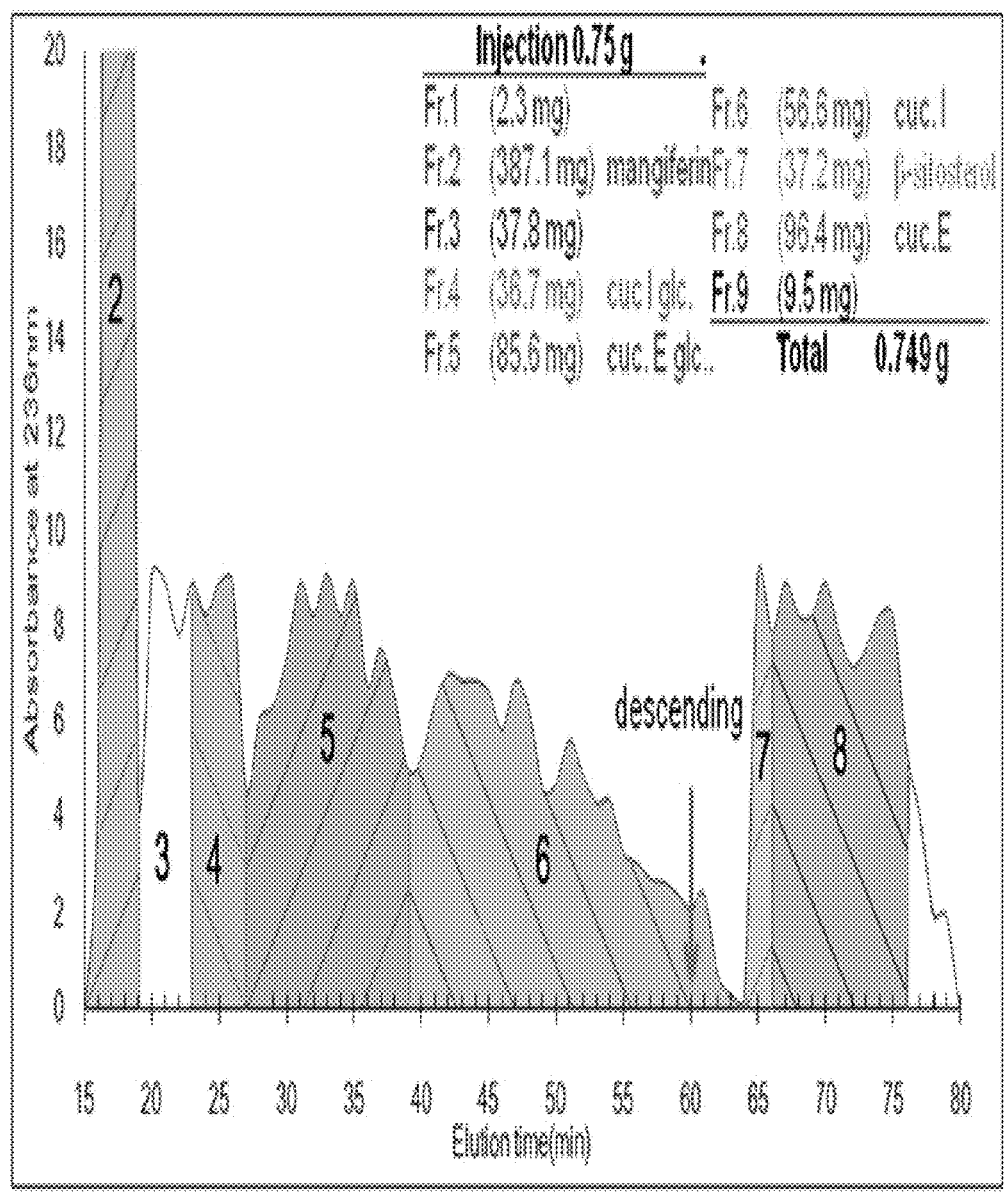
FIG. 8 shows the centrifugal partition chromatography diagram using chloroform-methanol-water solvent system wherein numbers 1-8 represent Fractions 1 to 8.

The ethyl acetate layer of methanol extract of *Aquilaria agallocha* Roxb hulls was obtained according to the materials and methods mentioned in Example 1. The solvent system containing chloroform-methanol-water (6:7:4, v/v/v) was used in the CPC. CPC is a method based on countercurrent chromatography (CCC). Separation is based on the differences in partitioning behavior of components between two immiscible liquids. The phase retained in the column is called the stationary phase, and the other one, the mobile phase. 0.75 g of the ethyl acetate of methanol extract of *Aquilaria agallocha* Roxb hulls was dissolved in 4 ml of chloroform-methanol-water. After 60 minutes of CPC, the organic phase was used as stationary phase and water was used as mobile phase with the flow rate 10.0 ml/min. After 60 minutes, the organic phase was used as the mobile phase. The centrifugation rate is 700 rpm. The ethyl acetate sample was subjected to the CPC for participation and then detected with UV detector (236 nm) (see FIG. 7). Nine fractions were obtained (see FIG. 8) wherein Fraction 1 was obtained in 0-14 minutes, Fraction 2 containing 82.49% magiferin was obtained in 15-18 minutes, Fraction 3 was obtained in 19-22 minutes, fraction 4 containing 73.54% curcurbitacin I glucoside was obtained in 23-26 minutes, Fraction 5 containing 63.24% curcurbitacin E glucoside was obtained in 27-38 minutes, Fraction 6 containing 80.09% curcurbitacin I was obtained in 39-63 minutes, Fraction 7 containing beta-sitosterol was obtained in 64-65 minutes, Fraction 8 containing 76.87% curcurbitacin E was obtained in 66-75 minutes and Fraction 9 was obtained in last 76-80 minutes.

| | | Peak area | | | |
|---|---|---|---|---|---|
| Hexane-EtOAc—MeOH—H₂O 12.24.16.9 | | | | | |
| | Rt | upper layer (before) | upper layer (after) | lower layer (after) | partition coefficient |
| cucurbitacin I glucoside | 21.735 | 262501 | 254542 | 7959 | 0.03 |
| cucurbitacin E glucoside | 29.324 | 507535 | 484438 | 23097 | 0.05 |
| cucurbitacin I | 29.891 | 563518 | 305630 | 167879 | 0.42 |
| cucurbitacin E | 37.035 | 825872 | 435677 | 390195 | 0.90 |

The recovery rate is 0.749 g and the recovery rate if 99.87%. Molecular sieve chromatography can be further used to increase purity of the above-mentioned compounds. Sephadex LH-20 gel (1.5 cm i.d.×36 cm) was used in the molecular sieve chromatography and methanol was used as the mobile phase. The purity of cucurbitacin I glucoside in Fraction 4 was increased from 73.54% to 92.57%, that of curcurbitacin E glucoside in Fraction 5 was increased from 63.24% to 90.24% and that of curcurbitacin I was increased from 80.09% to 95.36%. Since mangiferin is hard to dissolve in methanol, mangiferin in Fraction 2 was participated and then certrifugated to obtain mangiferin with an increased purity from 82.49% to 96.25%. Cucurbitacin E is hard to dissolvein water and methanol, Cucurbitacin E in Fraction 8 was participated and then certrifugated to obtain mangiferin with 96.87 purity.

What is claimed is:

1. A therapeutically effective amount of an aqueous *Aquilaria agallocha* woody hull of the fruit of *Aquilaria agallocha* extract for treating cancer wherein the extract is obtained by methanol extraction of *Aquilaria agallocha* followed by a partition with ethyl acetate and water, wherein the ethyl acetate layer is further eluted by a hexane-ethyl acetate mixture and methanol with silica column chromatography.

2. The extract of claim 1, wherein the ethyl acetate layer is eluted by mobile phases of (i) hexane-ethyl acetate mixture in a ratio of 1:0, 10:1, 10:2, 10:3, 10:4, 10:5, 10:6, 10:8, 1:1 and 0:1 and (ii) methanol with silica column chromatography so that 13 fractions are obtained.

3. The extract of claim 2, wherein Fractions 10:5 and 10:6 specifically contain cucurbitacin E and cucurbitacin I.

4. The extract of claim 2, wherein Fraction 3 (10:2) contains beta-sitosterol, Fraction 7 (10:5) contains genkwanin, Fraction 8 (10:5) contains cucurbitacin E, Fraction 9 (10:5) contains cucurbitacin I and cucurbitacin E glucoside, Fraction 11 (1:1) contains cucurbitacin I glucoside and Fraction 12 (0:1) contains genkwanin 5-0-glucoside and mangiferin.

5. The extract of claim 1, wherein the ethyl acetate layer is partitioned by centrifugal partition chromatography to obtain 9 fractions.

6. The extract of claim 4, wherein Fraction 2 contains magiferin, Faction 4 contains curcurbitacin I glucoside, Fraction 5 contains curcurbitacin E glucoside, Fraction 6 contains curcurbitacin I, Fraction 7 contains beta-sitosterol and Fraction 8 contains curcurbitacin E.

7. The extract of claim 6, wherein the fractions can be further purified by molecular sieve chromatography.

8. The extract of claim 1, wherein the aqueous *Aquilaria agallocha* woody hull of the fruit of *Aquilaria agallocha* extract is from *Aquilaria agallocha* Roxb.

9. A pharmaceutical formulation, consisting essentially of the extract of claim 1 and a pharmaceutically acceptable carrier.

10. The pharmaceutical formulation of claim 9, which is for oral, rectal, topical, buccal, parenteral or transdermal administration.

11. The pharmaceutical formulation of claim 10, which is in a form selected from the group consisting of cachet, lozenge, tablet, powder, granule, solution, suspension and emulsion.

* * * * *